US012758872B2

(12) United States Patent
Black et al.

(10) Patent No.: US 12,758,872 B2
(45) Date of Patent: Oct. 13, 2026

(54) ARTIFICIAL INTELLIGENCE DETERMINED EMOTIONAL STATE WITH DYNAMIC MODIFICATION OF OUTPUT OF AN INTERACTION APPLICATION

(71) Applicant: Sony Interactive Entertainment Inc., Tokyo (JP)

(72) Inventors: Glenn Black, San Mateo, CA (US); Steven Osman, San Mateo, CA (US)

(73) Assignee: Sony Interactive Entertainment Inc., Tokyo (JP)

(*) Notice: Subject to any disclaimer, the term of this patent is extended or adjusted under 35 U.S.C. 154(b) by 156 days.

(21) Appl. No.: 18/591,752

(22) Filed: Feb. 29, 2024

(65) Prior Publication Data

US 2025/0010180 A1 Jan. 9, 2025

Related U.S. Application Data

(60) Provisional application No. 63/512,569, filed on Jul. 7, 2023.

(51) Int. Cl.

| | |
|---|---|
| ***A63F 13/40*** | (2014.01) |
| ***A61B 5/16*** | (2006.01) |
| ***A63F 13/60*** | (2014.01) |
| ***G06N 20/00*** | (2019.01) |

(52) U.S. Cl.

CPC .............. *A63F 13/40* (2014.09); *A61B 5/165* (2013.01); *A63F 13/60* (2014.09); *G06N 20/00* (2019.01)

(58) Field of Classification Search

None

See application file for complete search history.

(56) References Cited

U.S. PATENT DOCUMENTS 9,031,293 B2 * 5/2015 Kalinli-Akbacak .... G06F 3/011 382/128

9,174,135 B2 * 11/2015 Abe ........................ A63F 13/92

9,943,758 B2 * 4/2018 Sato ...................... A63F 13/837

(Continued)

OTHER PUBLICATIONS

International Search Report and Written Opinion in International Appln. No. PCT/US2024/035644, mailed on Nov. 11, 2024, 10 pages.

(Continued)

*Primary Examiner* — Seng H Lim

(74) *Attorney, Agent, or Firm* — Fish & Richardson P.C.

(57) ABSTRACT

A method including receiving an input from a user for an interaction application that is executing. The method including receiving a first plurality of multimodal cues from a plurality of trackers, wherein each of the plurality of trackers is configured to track a corresponding cue using artificial intelligence. The method including providing the first plurality of multimodal cues to an artificial intelligence (AI) model configured to classify one or more emotions of a user, wherein the AI model generates a first predicted emotion based on the first plurality of multimodal cues. The method including determining a modification to content generated by the interaction application in response to the input, wherein the modification to the content is determined based on the predicted emotion. The method including providing the modification to the interaction application, wherein the interaction application is configured to generate modified content based on the modification.

19 Claims, 7 Drawing Sheets

(56) References Cited

U.S. PATENT DOCUMENTS

| | | | | |
|---|---|---|---|---|
| 10,706,674 | B2 | 7/2020 | Sorey et al. | |
| 10,835,823 | B2 | 11/2020 | Sumant et al. | |
| 11,176,484 | B1 | 11/2021 | Dorner | |
| 11,331,581 | B2 | 5/2022 | Pedersen et al. | |
| 11,373,446 | B1 | 6/2022 | Beisel | |
| 11,413,539 | B2 | 8/2022 | Aghdaie et al. | |
| 11,524,245 | B2 | 12/2022 | Osman et al. | |
| 11,544,524 | B2 * | 1/2023 | Seo | G06V 10/764 |
| 12,190,906 | B1 * | 1/2025 | Venkataraman | G10L 15/32 |
| 2011/0009193 | A1 * | 1/2011 | Bond | A63F 13/65 463/36 |
| 2011/0184721 | A1 * | 7/2011 | Subramanian | G10L 19/0018 704/4 |
| 2014/0112556 | A1 * | 4/2014 | Kalinli-Akbacak | G06V 40/176 382/128 |
| 2014/0206445 | A1 * | 7/2014 | Abe | A63F 13/26 463/31 |
| 2014/0223462 | A1 * | 8/2014 | Aimone | H04N 21/42201 725/10 |
| 2014/0324749 | A1 * | 10/2014 | Peters | G09B 7/04 706/46 |
| 2015/0328548 | A1 * | 11/2015 | Sato | A63F 13/63 463/31 |
| 2016/0210222 | A1 * | 7/2016 | Wyld | G06F 11/3672 |
| 2019/0201786 | A1 | 7/2019 | Muller | |
| 2019/0355209 | A1 | 11/2019 | Sorey et al. | |
| 2020/0104670 | A1 * | 4/2020 | Seo | G06V 10/764 |
| 2020/0202579 | A1 * | 6/2020 | Caballero | G06T 11/00 |
| 2020/0206631 | A1 * | 7/2020 | Sumant | A63F 13/55 |
| 2021/0187392 | A1 | 6/2021 | Kung et al. | |
| 2021/0192332 | A1 * | 6/2021 | Gangotri | G06N 3/0895 |
| 2022/0398411 | A1 * | 12/2022 | Cowen | G06F 18/41 |
| 2025/0307324 | A1 * | 10/2025 | Katsuhara | G16Y 20/40 |

OTHER PUBLICATIONS

Goncalves et al., "Enhancing intelligence in multimodal emotion assessments," Applied Intelligence, Sep. 2017, 46(2):470-86.

* cited by examiner

600

ARTIFICIAL INTELLIGENCE DETERMINED EMOTIONAL STATE WITH DYNAMIC MODIFICATION OF OUTPUT OF AN INTERACTION APPLICATION

CLAIM OF PRIORITY

The present application claims priority to and the benefit of the commonly owned, provisional patent application, U.S. Ser. No. 63/512,569, entitled "ARTIFICIAL INTELLIGENCE DETERMINED EMOTIONAL STATE WITH DYNAMIC MODIFICATION OF OUTPUT OF AN INTERACTION APPLICATION," with filing date of Jul. 7, 2023, which is herein incorporated by reference in its entirety.

TECHNICAL FIELD

The present disclosure is related to modifying content based on an emotion of a user, and more specifically to predicting emotion of a user using artificial intelligence, and modifying content of an interaction application based on the predicted emotion.

BACKGROUND OF THE DISCLOSURE

Video games and/or gaming applications and their related industries (e.g., video gaming) are extremely popular and represent a large percentage of the worldwide entertainment market. Video games are played anywhere and at any time using various types of platforms, including gaming consoles, desktop computers, laptop computers, mobile phones, etc.

A user's emotion can negatively influence gameplay of a video game. For instance, a user that is angry may not perform as well as when that user is calm. Instead of directing energy towards focusing on the game, that energy is wasted on feeling and exhibiting anger, which results in a loss of concentration that negatively impacts gameplay.

It is in this context that embodiments of the disclosure arise.

SUMMARY

Embodiments of the present disclosure relate to the identification of an emotion using artificial intelligence of a user interacting with an interaction application, and the modification of content, generated by the interaction application in response to input of the user, based on the emotion. Verification of the identified emotion is provided as feedback for training and updating a model using the artificial intelligence that is configured to identify emotion of the user.

In one embodiment, a method is disclosed. The method including receiving an input from a user for an interaction application that is executing. The method including receiving a first plurality of multimodal cues from a plurality of trackers, wherein each of the plurality of trackers is configured to track a corresponding cue using artificial intelligence. The method including providing the first plurality of multimodal cues to an artificial intelligence (AI) model configured to classify one or more emotions of a user, wherein the AI model generates a first predicted emotion based on the first plurality of multimodal cues. The method including determining a modification to content generated by the interaction application in response to the input, wherein the modification to the content is determined based on the predicted emotion. The method including providing the modification to the interaction application, wherein the interaction application is configured to generate modified content based on the modification.

In another embodiment, a non-transitory computer-readable medium storing a computer program for implementing a method is disclosed. The computer-readable medium including program instructions for receiving an input from a user for an interaction application that is executing. The computer-readable medium including program instructions for receiving a first plurality of multimodal cues from a plurality of trackers, wherein each of the plurality of trackers is configured to track a corresponding cue using artificial intelligence. The computer-readable medium including program instructions for providing the first plurality of multimodal cues to an artificial intelligence (AI) model configured to classify one or more emotions of a user, wherein the AI model generates a first predicted emotion based on the first plurality of multimodal cues. The computer-readable medium including program instructions for determining a modification to content generated by the interaction application in response to the input, wherein the modification to the content is determined based on the predicted emotion. The computer-readable medium including program instructions for providing the modification to the interaction application, wherein the interaction application is configured to generate modified content based on the modification.

In still another embodiment, a computer system is disclosed, wherein the computer system includes a processor and memory coupled to the processor and having stored therein instructions that, if executed by the computer system, cause the computer system to execute a method. The method including receiving a first plurality of multimodal cues from a plurality of trackers, wherein each of the plurality of trackers is configured to track a corresponding cue using artificial intelligence. The method including providing the first plurality of multimodal cues to an artificial intelligence (AI) model configured to classify one or more emotions of a user, wherein the AI model generates a first predicted emotion based on the first plurality of multimodal cues. The method including determining a modification to content generated by the interaction application in response to the input, wherein the modification to the content is determined based on the predicted emotion. The method including providing the modification to the interaction application, wherein the interaction application is configured to generate modified content based on the modification.

Other aspects of the disclosure will become apparent from the following detailed description, taken in conjunction with the accompanying drawings, illustrating by way of example the principles of the disclosure.

BRIEF DESCRIPTION OF THE DRAWINGS

The disclosure may best be understood by reference to the following description taken in conjunction with the accompanying drawings in which.

DETAILED DESCRIPTION

Figure 1:
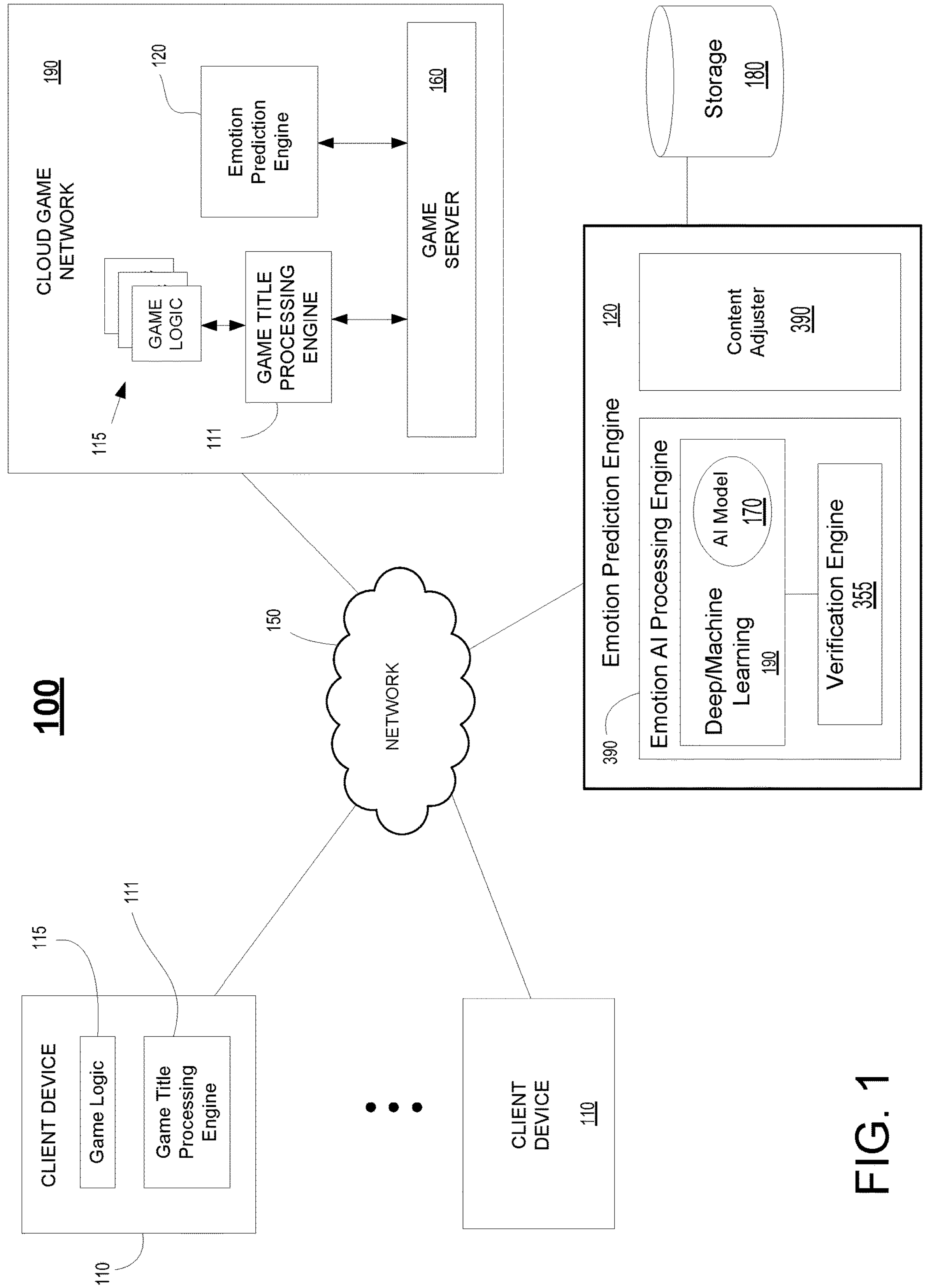
FIG. 1 illustrates a system configured for classification and/or identification of an emotion of a user using artificial intelligence (AI) and modification of content based on the identified emotion, and providing feedback indicating accuracy of the predicted emotion to update the artificial intelligence, in accordance with one embodiment of the present disclosure.

Although the following detailed description contains many specific details for the purposes of illustration, anyone of ordinary skill in the art will appreciate that many variations and alterations to the following details are within the scope of the present disclosure. Accordingly, the aspects of the present disclosure are set forth without any loss of generality to, and without imposing limitations upon, the claims that follow this description.

Generally speaking, the various embodiments of the present disclosure describe systems and methods for identifying the emotional state of a user, and making adjustments to inputs provided by the user or adjustments to execution and/or reaction of an interaction application (e.g., video game, metaverse, etc.) in response to the inputs and based on the identified emotional state. In one embodiment, a camera can view the face of the user or a partial face of the user using a VR headset. Other data of the user, including biometrics can also be collected. While the user is communicating verbally or via a controller, the emotion of the communicating user can be identified based on the collected data. In one embodiment, a machine learning model is configured to classify and/or identify the true emotional state of the player. In another embodiment, the machine learning model can be updated. For example, sometimes players play different types of games with different intensities. However, the intensity at which the player plays a game may not directly convey the emotional state of the player. For example, a player that is playing a fast racing game may appear to be angry, but instead the player is nervous. As such, the machine learning model is configured to identify the true emotional state through initial and later stages of training. In still another embodiment, an interaction application may be executed differently based on an identified emotion of a user. For example, an angry user may not be performing very accurately around technical turns when playing a race car video game. The system can adjust the speed or intensity of the video game to assist the user in response to different emotional states identified for the user when playing the video game. In another embodiment, the machine learning model and associated logic can be used to query the user to confirm a detected emotional state. The system can ask the user "are you angry?" If the user responds in the negative, then the system will train its model to avoid false positive identification of anger for that specific user, and in some implementations for the specific context of the game experienced by the user. If the user responds in the positive, then the system can train its model to reinforce the positive identification of anger. In some embodiments, other inputs (e.g., biometric sensor data) can be used to identify the emotion of the player, such as pupil dilation, blinking at high rates, eye movement, stress, increased heart rate, and the like. These indicators can be blended together to infer the emotional state of a player and provide for adjustment to gameplay. In some embodiments, based on identified emotion of a user various game parameters can be adjusted and/or modified, such as adjusting game lighting, or adjusting intensity of game characters and/or non-player characters (NPCs), adjusting physics affecting movement, etc. In some embodiments, the system can ask the user if an adjustment that has been automatically made is helpful, or whether the user wishes to avoid automatic adjustment of the gameplay. This provides the user with a mode for controlling how, when, and when not to modify game input/output dynamically.

Advantages of the methods and systems configured to identify emotional state of a user using an AI model include modification of content of an interaction application based on the emotional state, and the dynamic updating of the AI model based on feedback indicating accuracy of the identified emotion. In that manner, an interaction application executing in response to user input can be dynamically adjusted based on the emotional state of the user, such as making a game harder or easier, adjusting presentation of the user to others in a virtual environment (e.g., gaming environment, metaverse, etc.), adjusting communication of the user to disguise an emotional state of a corresponding user, etc. Still another advantage includes dynamic behavior modification of the user, as the user can be guided towards a beneficial emotional state (i.e., user or system specified) when interacting with an interaction application based on continued monitoring and identification of emotional state. Still other advantages include improved user experiences over time, because the AI model is dynamically updated with real-time feedback.

Throughout the specification, the reference to "game" or video game" or "gaming application" is meant to represent any type of interactive application that is directed through execution of input commands. For illustration purposes only, an interactive application includes applications for gaming, word processing, video processing, video game processing, etc. Also, the terms "virtual world" or "virtual environment" or "metaverse" is meant to represent any type of environment generated by a corresponding application or applications for interaction between a plurality of users in a multi-player session or multi-player gaming session. Further, the terms introduced above are interchangeable.

With the above general understanding of the various embodiments, example details of the embodiments will now be described with reference to the various drawings.

FIG. 1 illustrates a system 100 including an emotion prediction engine 120 including an AI model 170 that provides for classification and/or identification of emotion (i.e., emotional state) of a user, the modification of content of an interaction application responding to user input based on the identified emotion, and the dynamic updating of the AI model with feedback indicating accuracy of the identified emotion. In that manner, the AI model is continually updated to adapt to the user.

As shown, system 100 may provide gaming over a network 150 for one or more client devices 110. In particular, system 100 may be configured to enable users to interact with interaction applications, including provide gaming to users participating in a single-player or multi-player gaming sessions (e.g., participating in a video game in single-player or multi-player mode, or participating in a metaverse generated by an application with other users, etc.) via a cloud game network 190, wherein the game can be executed locally (e.g., on a local client device of a corresponding user) or can be executed remotely from a corresponding client device 110 (e.g., acting as a thin client) of a corresponding user that is playing the video game, in accordance with one embodiment of the present disclosure. In at least one capacity, the cloud game network 190 supports a multi-player gaming session for a group of users, to include delivering and receiving game data of players for purposes of coordinating and/or aligning objects and actions of players within a scene of a gaming world or metaverse, managing communications between user, etc. so that the users in distributed locations participating in a multi-player gaming session can interact with each other in the gaming world or metaverse in real-time. In another capacity, the cloud game network 190 supports multiple users participating in a metaverse.

In one embodiment, the cloud game network 190 may support artificial intelligence (AI) based services including chatbot services (e.g., ChatGPT, etc.) that provide for one or more features, such as conversational communications, composition of written materiel, composition of music, answering questions, simulating a chat room, playing games, and others.

Users access the remote services with client devices 110, which include at least a CPU, a display and input/output (I/O). For example, users may access cloud game network 190 via communications network 150 using corresponding client devices 110 configured for providing input control, updating a session controller (e.g., delivering and/or receiving user game state data), receiving streaming media, etc. The client device 110 can be a personal computer (PC), a mobile phone, a personal digital assistant (PAD), handheld device, etc.

In one embodiment, as previously introduced, client device 110 may be configured with a game title processing engine and game logic 115 (e.g., executable code) that is locally stored for at least some local processing of an application, and may be further utilized for receiving streaming content as generated by the application executing at a server, or for other content provided by back-end server support.

In another embodiment, client device 110 may be configured as a thin client providing interfacing with a back end server (e.g., game server 160 of cloud game network 190) configured for providing computational functionality (e.g., including game title processing engine 111 executing game logic 115—i.e., executable code—implementing a corresponding application). In particular, client device 110 of a corresponding user is configured for requesting access to applications over a communications network 150, such as the internet, and for rendering for display images generated by a video game executed by the game server 160, wherein encoded images are delivered (i.e., streamed) to the client device 110 for display. For example, the user may be interacting through client device 110 with an instance of an application executing on a game processor of game server 160 using input commands to drive a gameplay. Client device 110 may receive input from various types of input devices, such as game controllers, tablet computers, keyboards, gestures captured by video cameras, mice, touch pads, audio input, etc.

In addition, system 100 includes an emotion prediction engine 120 including an emotion AI processing engine 390 that is configured to classify and/or identify emotion of a user interacting with an interaction application (e.g., video game, metaverse, etc.) using a artificial intelligence. The emotion prediction engine 120 may be implemented at the back-end cloud game network, or as a middle layer third party service that is remote from the client device. In some implementations, the emotion prediction engine 120 may be located at a client device 110. The classification and/or identification and/or prediction of emotion of a user may be performed using artificial intelligence (AI) via an AI layer. For example, the AI layer may be implemented via an AI model 170 as executed by a deep/machine learning engine 190 of the gesture prediction engine 120.

Content adjuster 390 is configured to determine modification of content based on the identified emotion, wherein the content is generated by the interaction application responsive to user input. The verification engine 355 is configured to verify accuracy of the identified emotion, wherein verification information is provided as feedback for continued training of the AI model 170 that is configured to identify emotion of the user. For example, verification engine 355 is configured to determine when the classification of emotion for a user is incorrect based on one or more multimodal cues, wherein feedback when the classification is correct and/or incorrect is used to update and/or train the AI model to continually adapt to the user. Storage 180 may be used for storing information, such as information related to the feedback and/or data used for building the AI model 170.

Figure 2:
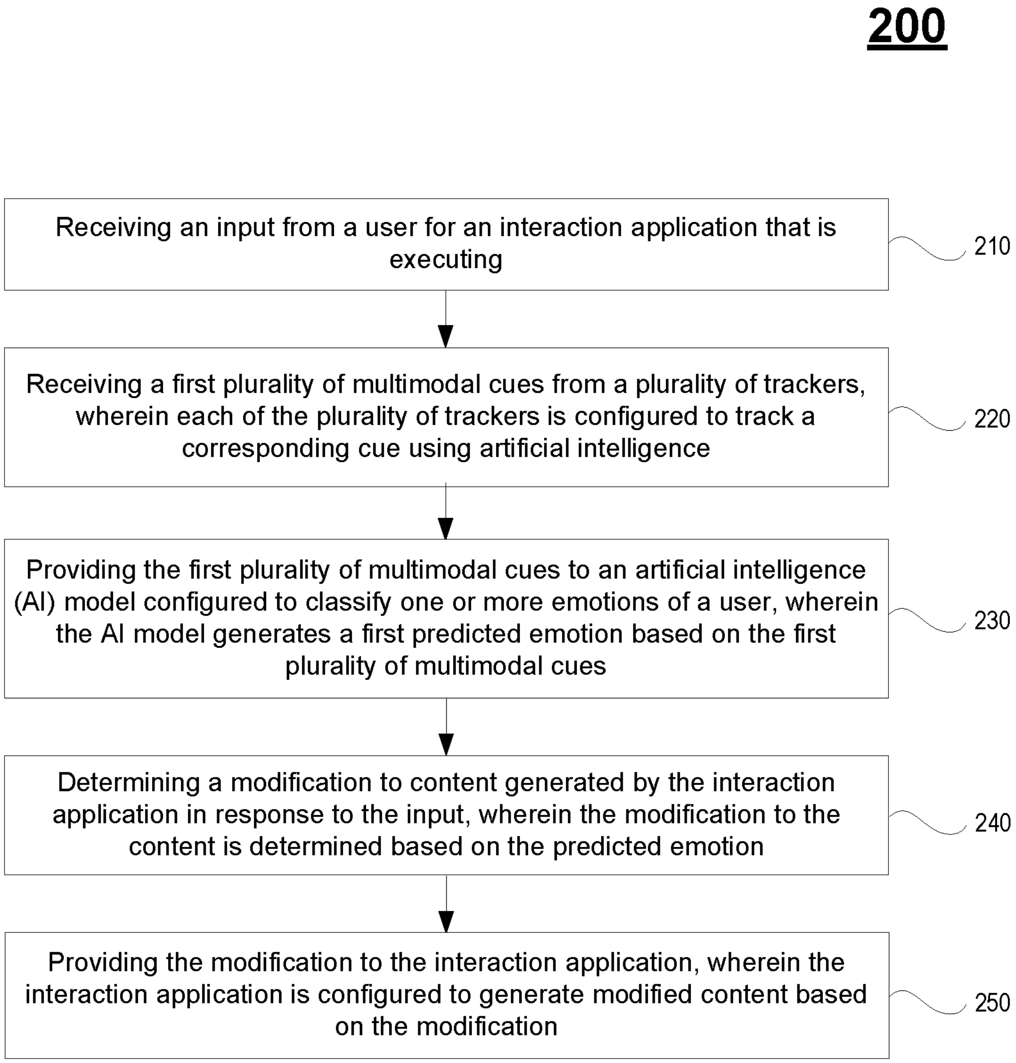
FIG. 2 is a flow diagram illustrating a method for classification of an emotion of a user interacting with an interaction application using an AI model and the modification of content based on the identified emotion, in accordance with one embodiment of the present disclosure.

With the detailed description of the system 100 of FIG. 1, flow diagram 200 of FIG. 2 discloses a method for classification and/or identification of an emotion of a user interacting with an interaction application using an AI model receiving multimodal cues of the user, and the modification of content based on the identified emotion, in accordance with one embodiment of the present disclosure. The operations performed in the flow diagram may be implemented by one or more of the entities previously described components, and also system 100 described in FIG. 1, including emotion prediction engine 120.

At 210, the method includes receiving an input from a user for an interaction application that is executing. The user interacts with the interaction application by providing input for execution by the interaction application. The interaction application can be any application, and includes a video game, or an application providing virtual reality, such as a metaverse. Generally, the interaction application generates a virtual world within which the user can participate. For example, the user is able to interact with the virtual world (e.g., navigating, selecting, communicating, etc.) using input.

At 220, the method includes receiving a first plurality of multimodal cues from a plurality of trackers. Each of the plurality of trackers captures relevant data one or more sources that relate to the user, or the environment surrounding the user, or the gaming environment (e.g., game context), used for determining emotion of the user. For example, relevant data may include biometric data of the user, audio data of the user or environment, intensity data regarding use of devices (e.g., keyboard, etc.), camera views, eye tracking data, face tracking data, etc. Further, a corresponding tracker is configured to track a corresponding cue using artificial intelligence, wherein the cue is designed to focus on one preselected aspect regarding the user, or the user's environment, or the gaming environment. One or more cues may be analyzed to determine an emotion of the user. For example, a tracker may receive camera views of the user's face, spatial orientation data of the user's head, eye tracking data, and others to determine in which direction the user is viewing a virtual environment generated by the interaction application. In another example, a tracker may receive different data to determine when a finger of the use is moving and how fast the finger is moving. In still another example, a tracker may receive one or more biometric data (e.g., heart rate, perspiration, rate of breathing, movement, twitchiness, etc.) to determine a degree of focus of the user while interacting with the interactive application. Still other trackers are supported.

At 230, the method includes providing the first plurality of multimodal cues to an artificial intelligence (AI) model to determine a current emotion of the user. The AI model is configured to classify one or more emotions of a user. For instance, the AI model classifies a first predicted emotion based on the first plurality of multimodal cues.

At 240, one or more actions can be taken once the predicted emotion has been identified. In particular, the method includes determining a modification to content generated by the interaction application in response to the input, wherein the modification to the content is determined based on the predicted emotion. The content may be generated by the interaction application in response to user input. As such, identification of the content and how to modify the content based on the predicted emotion is necessary in order to guide the user in a way to ameliorate or enhance the emotional state of the user using the modified content.

At 250, the method includes providing the modification to the interaction application, wherein the interaction application is instructed to generate modified content based on the modification. For example, content may be modified to guide the user away from the predicted emotion, such as by providing gaming music that is less intense when the predicted emotion indicates the user is angry. Other examples of content modification include changing a game parameter, changing communication of a user, generating an overlay including modified content, changing a UI directly or using an overlay, etc.

Figure 3:
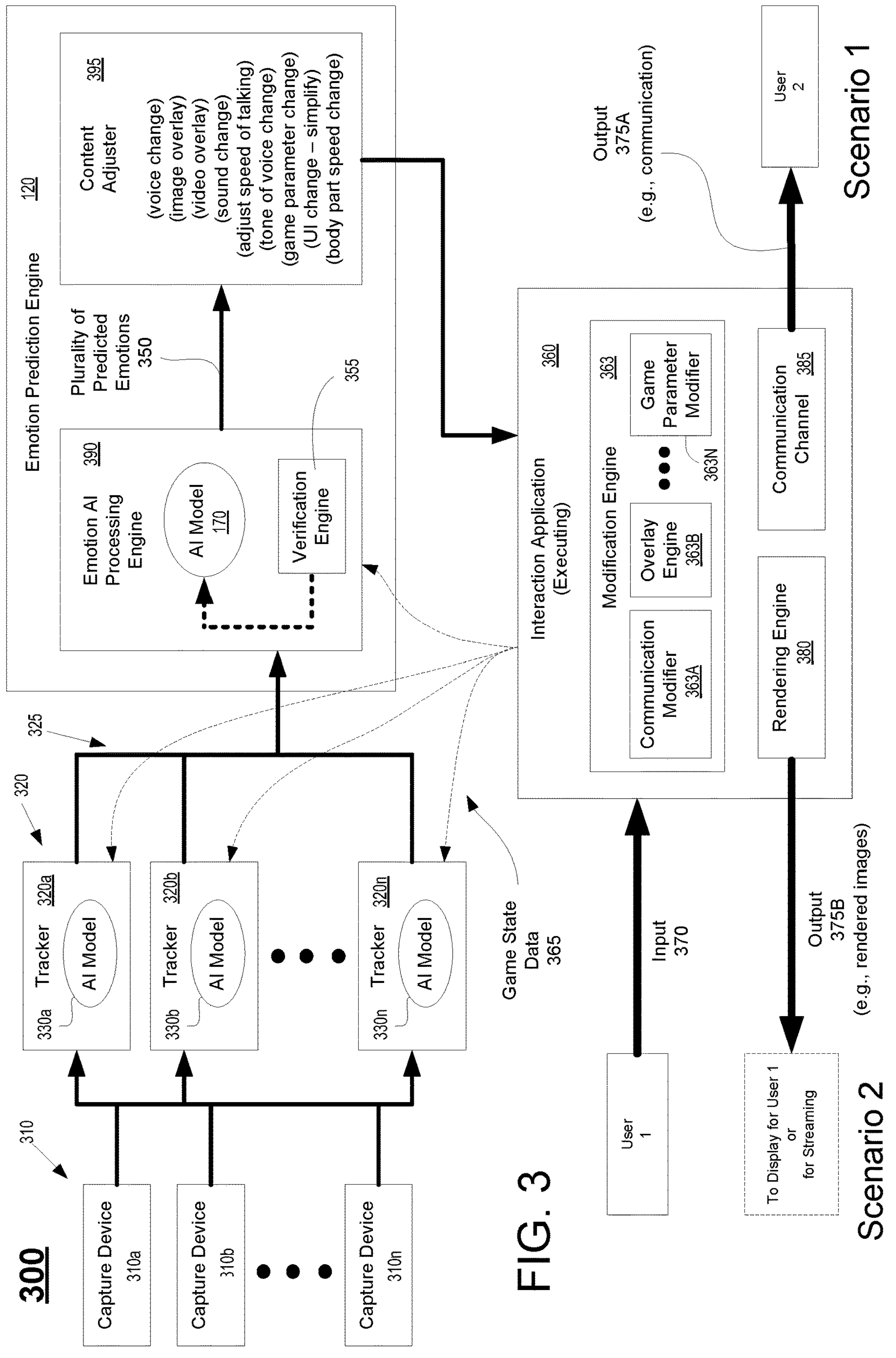
FIG. 3 is an illustration of a system configured to implement an AI model configured for classifying and/or identifying an emotion of a user interacting with an interaction application and the modification of content based on the identified emotion, and using feedback indicating accuracy of the identified emotion to train and update the AI model, in accordance with one embodiment of the present disclosure.

FIG. 3 is an illustration of a system configured to implement an AI model configured for classifying and/or identifying an emotion of a user interacting with an interaction application and the modification of content based on the identified emotion, and using feedback indicating accuracy of the identified emotion to train and update the AI model, in accordance with one embodiment of the present disclosure. The operations performed in the flow diagram may be implemented by one or more of the entities previously described components, and also system 100 described in FIG. 1. For purposes of illustration, FIG. 3 is described within the context of a third party or mid-level emotion prediction engine communicatively coupled through a network, although it is understood that the operations performed within system of FIG. 3 can be performed by the cloud based network 190 or the client device 110 of FIG. 1.

A plurality of capture devices 310, including capture devices 310*a* through 310*n*, is shown within the surrounding environment of a communicator. Each of the capture devices is configured to capture data and/or information related to a user or the surrounding environment around the user. For example, a capture device may capture biometric data of the user, and include cameras pointed at the user, biometric sensors, microphone, hand movement sensors, finger movement sensors, etc. Purely for illustration purposes, biometric data captured by the capture devices 310 may include heart rate, facial expressions, eye movement, intensity of input provided by the user, speed of audio communication, audio of communication, intensity of audio communication, etc. In addition, capture devices may capture other related information, including information about the environment within which the user is located. For example, capture devices may include cameras and/or ultra-sonic sensors for sensing the environment, cameras and/or gyroscopes for sensing controller movement, microphones for detecting audio from the communicator or devices used by the communicator or the intensity of use of those devices, etc.

The information captured by the plurality of capture devices 310 is sent to one or more of the plurality of trackers 320 (e.g., trackers 320*a-n*). Each of the plurality of trackers includes a corresponding AI model configured for performing a customized classification of data, which is then output as telemetry data 325 and received by the emotion prediction engine 120. The telemetry data may be considered as multimodal cues, wherein each tracker provides a unique multimodal cue, and wherein one or more multimodal cues may be used to classify (i.e., predict) an emotion of a user and/or to determine whether a classified or predicted emotion has been correctly predicted.

For example, tracker 320*a* includes AI model 330*a*, tracker 320*b* includes AI model 330*b*, and tracker 320*n* includes AI model 330*n*. In particular, each of the trackers collects data from one or more capture devices 310, and is configured to perform a customized function by analyzing captured data to determine a corresponding multimodal cue or factor useful in determining emotion of a user. For example, a customized function may be to determine in which direction the eyes of the communicator are pointed, or eye movement, and may collect data from one or more capture devices, including eye tracking cameras, head motion trackers, etc. In this case, the customized AI model in a corresponding tracker is configured to analyze the data and determine gaze direction. Other customized functions provided as multimodal cues include intensity of use of devices, or tracking a certain behavior, or tracking body movement (e.g., fingers, hands, arms, legs, face, head, etc.), tracking game state of a video game 365, determining game context of a video game based on game state 365, etc.

As such, capture devices 310 may capture information useful in determining one or more customized functions (e.g., determining multimodal cues useful in classifying emotion of a user), such as, facial cameras to perform tracking of portions of the face (e.g., to determine facial expressions); biometric sensors to capture heart rate, facial expressions, eye movement, rate of sweating, rate of breathing, etc.; movement sensors to capture hand or finger movement and intensity or speed of the movement, controller movement, etc.; audio receivers to capture audio uttered from the communicator (e.g., intensity, speed, etc.), or generated by the communicator (e.g., keyboard usage intensity, intensity of input provided by the communicator), or of the surrounding environment, etc.

Further, other information may be captured and delivered to the trackers 320, including user saved data used to personalize a video game for the corresponding user (e.g., character information and/or attributes used to generate a personalized character, user profile data, etc.), and metadata configured to provide relational information and/or context for other information, such as game state data 365 (e.g., of a video game that is the interaction application) and the user saved data. For example, the game state may be from a game play of a video game at a particular point in time, or a state of an application during execution, wherein game state data allows for the generation of the gaming environment at the corresponding point in the game play. For example, game state data may include states of devices used for rending the game play (e.g., states of the CPU, GPU, memory, register values, etc.), identification of the executable code to execute the video game at that point, game characters, game objects, object and/or game attributes, graphic overlays, and other information. Also, the metadata may include information describing the game context of a particular point in the game play of the user, or the metadata may be used to determine game context, such as where in the game the user is, type of game, mood of the game, rating of game (e.g., maturity level), the number of other players there are in the gaming environment, game dimension displayed, which players are playing a particular gaming session, descriptive information, game title, game title version, franchise, format of game title distribution, downloadable content accessed, links, credits, achievements, awards, trophies, and other information. The game state and/or metadata may be used for predicting the emotion of a user and/or to verify that a predicted emotion is correct, by determining game context based on the game state and determining whether the corresponding predicted emotion is consistent with the game context. In other embodiments, the game state and/or game context may be included as one of the multimodal cues delivered to the emotion prediction engine 120 and used for determining whether a predicted emotion is correct.

As shown, the multimodal cues 325 are delivered to the emotion prediction engine 120, and more specifically to the emotion AI processing engine 390, which includes a customized AI model 170 configured to classify emotion of the user. In particular, the AI model 170 is configured to analyze the multimodal cues 326 continuously provided as input and classify and/or identify and/or predict one or more emotions of the user (e.g., happy, angry, satisfied, unsatisfied, frustrated, etc.). That is, AI model 170 outputs a plurality of predicted emotions 350 of the user.

Further, the emotion prediction engine 120 includes a verification engine 355 configured to provide feedback on a selected predicted emotion 350. The accuracy of a selected predicted emotion can be determined through analysis of the multimodal cues 325 (including game state and game context), including cues delivered post classification of the predicted emotion. The greater the number of multimodal cues used for verification may provide for a more accurate determination on whether the predicted emotion accurate. Accuracy may be determined through indirect inference, and/or direct inference (e.g., through querying of the user), and/or through relational connections between indirect and direct inferences. Information regarding the accuracy of the predicted emotion can be provided as feedback to the AI model 170 for training and/or updating of the AI model. With continued feedback and updating, gradually the AI model is trained to more accurately classify a predicted emotion for the user. For example, an updated predicted emotion may be classified based on the updated AI model 170.

The emotion prediction engine 120 includes a content adjuster 395 configured to modify content generated by the interaction application 360 that is executing based on the predicted emotion. The interaction application initially generates the content based on user input 370. In one embodiment, the content adjuster 395 only identifies the content and the manner in which the content is suitably modified based on a predicted emotion. In another embodiment, the content adjuster also modifies at least a portion of the content. An instruction for modifying the content is delivered from the content adjuster 395 to the interaction application 360, wherein the instruction indicates the content and manner in which to apply a modification to the content (e.g., change game parameter, produce overlay, etc.).

The interaction application 360 using the modification engine 363 is configured to modify content originally generated in response to user input 370 (e.g., from user 1). In particular, the modification engine 363 includes one or more modifiers 363A through 363N, each of which is configured to generate modified content. For purposes of illustration, the content may be modified using different techniques, including changing voice, providing an image or video overlay, producing a sound or music change, adjust a speed of talking, changing a tone of voice, changing a game parameter, changing a UI, changing motion of a body part (e.g., speed of movement), etc.

For example, game parameter modifier 363N is configured to modify a parameter of a video game, or an application (e.g., metaverse, etc.). This is labeled as "Scenario 2", wherein user 1 is interacting with and controlling interaction application 360, such as by providing input 370 to drive execution of a video game, including influencing the generation of rendered video frames by the rendering engine 380 and provided as output 375B for display to user 1 or used for streaming. The game parameter may be modified to help the user be more successful in a game play of a video game, such as when the predicted emotion indicates the user is angry or frustrated and is unable to play the video game effectively. For instance, modification of the game parameter allows the video game to be easier to play through a section, or may offer the user an easier task (quest 2 over quest 1) to accomplish rather than an expected task (quest 1) in the game play that may be more difficult. Or if the predicted emotion indicates the user is bored, the game parameter may be modified to make the game harder to play, or to present a harder task to accomplish.

Further, communication modifier 363A is configured to modify a communication made by a user, wherein the communication is directed to a target user (e.g., user 2). This is labeled as "Scenario 1", wherein communication content is modified as it passes through the interaction application 360. In particular, a user may be providing as input a verbal communication (e.g., user 1 providing the communication as input 370) that is directed to a target user (e.g., user 2). The interaction application generates content that may be a translation (e.g., to another format) of the input communication for delivery to the target user over a communication channel 385, or may just pass the communication along without any translation, wherein the channel 385 communicatively couples user 1 and user 2. The input communication that is translated (e.g., optionally) may reflect an angry user (i.e., when the predicted emotion indicates that user 1 is angry), and may be offensive to the target user. In this case, the modified content includes a modification of the communication, that may be translated, such as toning down the nature of the communication, or modifying the communication to be less offensive. The modified communication, that may be translated, is delivered as output 375A to the target user (e.g., user 2).

In another example, overlay engine 363B is configured to generate an overlay that includes the modified content, wherein the overlay is incorporated into one or more video frames generated by the interaction application to replace the original content. For example, the overlay including the modified content may be overlaid a portion of a rendered video frame including the content, that is provided as output 375B for display or streaming. As an illustration, an angry user reflected with an angry avatar may be overlaid with a representative avatar that has an emotion that is disguised to show a different emotion (e.g., happy, sad, etc.) than the predicted emotion indicating the user is angry. In still another example, a user interface (UI) may be modified based on the predicted emotion. For instance, if the predicted emotion indicates the user is angry or frustrated and too impatient or distracted to interact with a UI that is complicated, the UI may be modified to a simpler version, wherein the modified UI may be generated by overlay engine 363B, or the interaction application 360 may be influenced by a game parameter change to simplify the UI.

Figure 4:
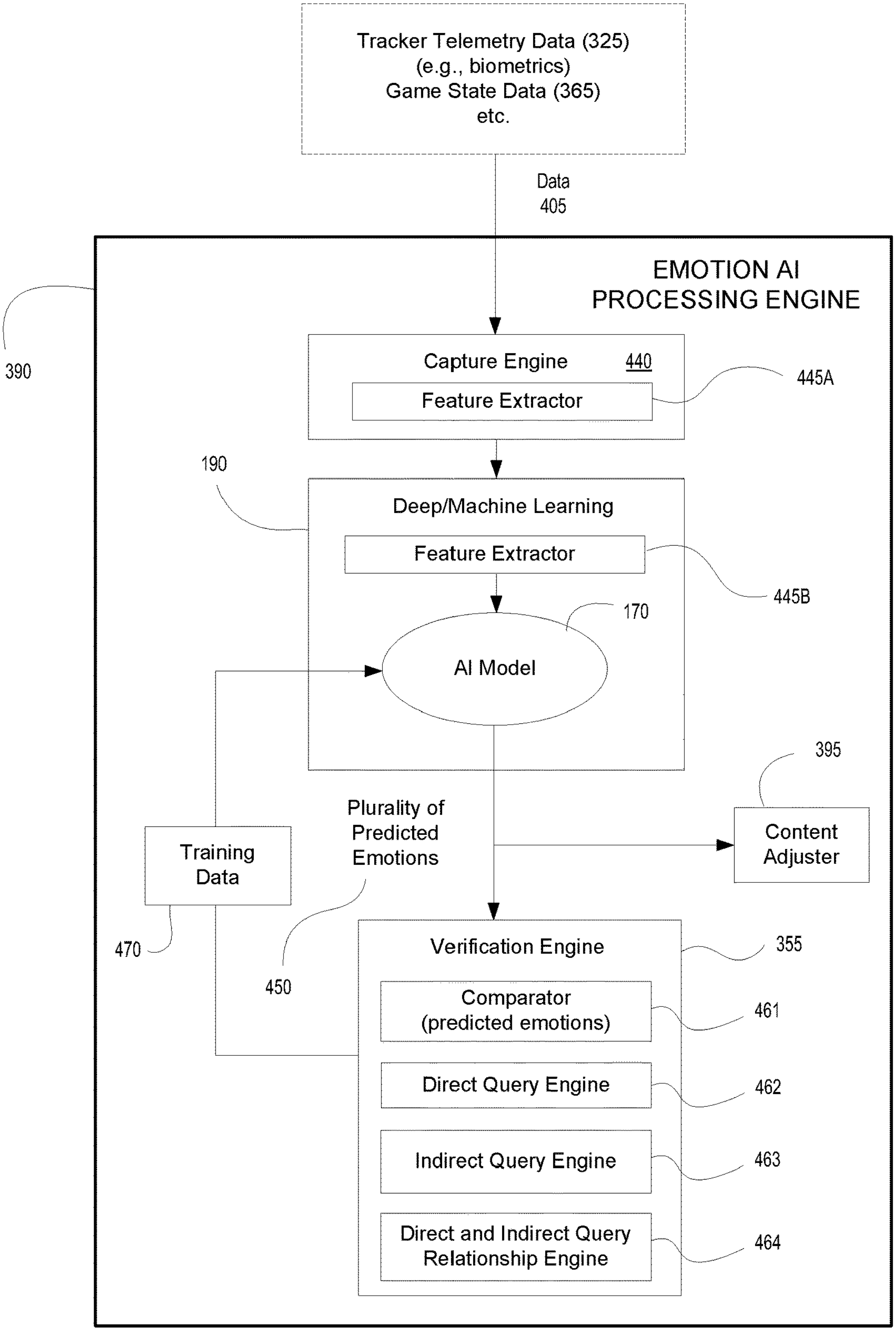
FIG. 4 is an illustration of an emotion processing engine configured to classifying and/or identifying an emotion of a user interacting with an interaction application and the modification of content based on the identified emotion using an AI model, and determine that the identification is incorrect, which can be fed back to the AI model for updating, in accordance with one embodiment of the present disclosure.

FIG. 4 is an illustration of an emotion AI processing engine 390 configured for classifying and/or identifying and/or predicting an emotion of a user interacting with an interaction application using an AI model 170, and the modification of content based on the predicted emotion using content adjuster 395, and determining accuracy of the predicted emotion, which can be fed back to the AI model for updating, in accordance with one embodiment of the present disclosure.

Capture engine 440 of the gesture prediction engine 120 may be configured to receive various data 405 through a network relevant to predicting (i.e., classifying) an emotion of a user, and to verify that the prediction is correct. As previously described, the received data 405 may include telemetry data 325 (e.g., biometrics, etc.) from the plurality of trackers 320, game state data 365 and/or game state data 365 from an executing application (e.g., video game, metaverse, etc.), user saved data, metadata, and/or information.

The capture engine 440 is configured to provide input into the AI model 170 for classification of emotion of a user. As such, the capture engine 340 is configured to capture and/or receive as input any data that may be used to identify and/or classify emotion of the user, and/or to verify that the predicted emotion is correct (i.e., verify accuracy of the predicted emotion). Selected portions of the captured data may be analyzed to identify and/or classify the emotion. In particular, the received data 405 is analyzed by feature extractor 445A to extract out the salient and/or relevant features useful in classifying and/or identifying emotion of the user. The feature extractor may be configured to learn and/or define features that are associated with emotions that are known, or portions thereof. In some implementations, feature definition and extraction is performed by the deep/machine learning engine 190, such that feature learning and extraction is performed internally, such as within the feature extractor 445B.

As shown, the deep/machine learning engine 190 is configured for implementation to classify and/or identify and/or predict an emotion of a corresponding user. In one embodiment, the AI model 170 is a machine learning model configured to apply machine learning to classify/identify/predict the emotion of the user. In another embodiment, the AI model is a deep learning model configured to apply deep learning to classify/identify/predict the emotion of the user, wherein machine learning is a sub-class of artificial intelligence, and deep learning is a sub-class of machine learning.

Purely for illustration, the deep/machine learning engine 190 may be configured as a neural network used to implement the AI model 170, in accordance with one embodiment of the disclosure. Generally, the neural network represents a network of interconnected nodes responding to input (e.g., extracted features) and generating an output (e.g., classify or identify or predict the intent of the performed gesture). In one implementation, the AI neural network includes a hierarchy of nodes. For example, there may be an input layer of nodes, an output layer of nodes, and intermediate or hidden layers of nodes. Input nodes are interconnected to hidden nodes in the hidden layers, and hidden nodes are interconnected to output nodes. Interconnections between nodes may have numerical weights that may be used link multiple nodes together between an input and output, such as when defining rules of the AI model 170.

In particular, the AI model 170 is configured to apply rules defining relationships between features and outputs (e.g., biometric corresponding to a particular emotion, etc.), wherein features may be defined within one or more nodes that are located at one or more hierarchical levels of the AI model 170. The rules link features (as defined by the nodes) between the layers of the hierarchy, such that a given input set of data leads to a particular output (e.g., event classification 350) of the AI model 170. For example, a rule may link (e.g., using relationship parameters including weights) one or more features or nodes throughout the AI model 170 (e.g., in the hierarchical levels) between an input and an output, such that one or more features make a rule that is learned through training of the AI model 170. That is, each feature may be linked with one or more features at other layers, wherein one or more relationship parameters (e.g., weights) define interconnections between features at other layers of the AI model 170. As such, each rule or set of rules corresponds to a classified output. In that manner, the resulting output 450 according to the rules of the AI model 170 may classify and/or label and/or identify and/or predict an emotion of a user, wherein the output 450 includes one or more predicted emotions 450, such that the AI model continually receives input data and outputs emotions of the user.

Further, the output (e.g., a selected predicted emotion 450) from the AI model 170 may be used to determine a course of action to be taken as determined by the content adjuster 395, as previously described. For example, a game parameter may be changed to change how a video game is played based on a predicted emotion, or an overlay is generated including modified content based on a predicted emotion, or a communication is modified based on a predicted emotion, or an instruction from a user to a video game is modified based on a predicted emotion, etc.

As shown, the emotion AI processing engine 390 is also configured to perform verification of the accuracy of the predicted emotion, and providing feedback to the AI model 170 indicating the accuracy (accurate or inaccurate) for training the AI model 170, wherein the AI model is updated based on the feedback. In particular, after a predicted emotion is generated by the AI model 170, additional data may be collected and delivered to the verification engine 355 to determine accuracy of the predicted emotion. The additional data may include data 405 that is updated, including telemetry data 325 from the plurality of trackers 320, game state data 365, metadata, etc.

The feedback can be determined through indirect or direct inferences, or a combination of both providing relational inferences between the two. Further, each of the techniques may be used to confirm results, such as making an indirect inference as to emotion to confirm a direct inference, or vice versa, thus providing a relational connection between the two types of inferences.

In particular, the verification engine 355 includes a comparator 461 configured for comparing predicted emotions, a direct query engine 462 for directly querying the user about the accuracy of a predicted emotion, an indirect query engine 463 for indirectly querying the user about the accuracy of a predicted emotion, and a relationship engine 464 that provides a relational connection between a direct inference and an indirect inference regarding accuracy of a corresponding predicted emotion.

The comparator 143 is configured to compare predicted emotions for verifying accuracy. For instance, a predicted emotion may be classified using a first set or plurality of multimodal cues, wherein the first set of cues are captured or determined within a first time period. A subsequent predicted emotion may be classified using a second set or plurality of multimodal cues captured within a second time period after the first time period. Further, the first second set of multimodal cues is captured within a threshold time period from the capture of the first set of multimodal cues to ensure that the predicted emotion and the subsequent predicted emotion are similar, and that they can be directly correlated with each other. In that manner, if the subsequent predicted emotion is consistent with the predicted emotion (i.e., similar or the same), then the accuracy of the predicted emotion has a high degree of confidence (i.e., the prediction is accurate). On the other hand, if the subsequent predicted emotion is consistent with the predicted emotion (i.e., not similar, or not the same), then the accuracy of the predicted emotion has a low degree of confidence (i.e., the prediction is inaccurate).

Other techniques or approaches may be used to determine accuracy of a predicted emotion. In some implementations, the comparator includes an AI model to perform verification of the accuracy of the predicted emotion. For example, accuracy may be determined through analysis of game context. A predicted emotion may not align with a determined game context, and as such is deemed inaccurate or is given a lower degree of confidence. However, if the predicted emotion aligns with a determined game context, then the predicted emotion has a higher degree of confidence.

A determination that the predicted emotion is correct or incorrect by the verification engine 355 may be directly determined or inferred or indirectly inferred, or a combination of both for relational purposes. For example, during initial stages of training the AI model 170 that is learning to adapt to the user, a more direct approach may be taken. Normally, direct queries are used with caution in order to minimize interruptions with the communicator. However, direct queries can be used to quickly train the AI model, such that as the AI model continually gets updated. In another example, when it is determined that the predicted emotion has a low or very low degree of confidence (i.e., indicating that the AI model cannot predict an emotion of the user accurately), then the direct approach may be taken. In particular, the direct query engine 145 may directly query the user whether or not the predicted emotion is accurate. The response from the user is then fed back to the AI model 170 for training and updating.

The direct approach may be combined with an indirect approach for relational purposes, such that the indirect approach may be used by the indirect query engine 463 to infer whether the predicted emotion is correct or not. For instance, the indirect approach may be to query the user to select between two or more options, or to perform one of a selection of tasks, or whether or not to perform a single task. Selection of certain tasks (e.g., side quests, questions, etc.) or whether or not to perform a single task may indicate (as confirmed with results from the direct approach) accuracy of the predicted emotion. For example, if the predicted emotion indicates that the user is frustrated or angry while interacting with the interaction application, then the user may not want to perform a single task (e.g., thinks it is a waste of time) or may select a task from a group of tasks that promotes that anger (e.g., a task that feeds on the anger).

Specifically, direct and indirect inferences can be combined to determine a positive connection or relationship between the two inferences, as implemented by the relationship engine 464. For instance, when the user confirms a predicted emotion (e.g., through direct inference), then the indirect inference may also accurately confirm the predicted emotion. In particular, a user may be presented for selection a first and second option (e.g., a first task and second task, or first and second quests, etc.). The options are presented in combination with positive affirmation of the predicted emotion from the user (i.e., direct inference). A selection is received from the user, and a positive relationship between the predicted emotion and the selection between the first or second options by the user can be made, especially with further confirmation using the direct inference.

Thereafter, for a subsequent predicted emotion is made, and the first and second options are presented to the user, then a subsequent selection between the first option and the second option can be used to determine accuracy of a subsequent predicted emotion, based on the relationship between the predicted emotion and the selection, especially when the predicted emotion and the subsequent prediction emotion are closely correlated (e.g., similar). That is, a later implementation of the indirect approach may be in isolation (i.e., not using the direct inference) to determine whether a future predicted emotion is accurate. Specifically, while the direct approach is straightforward with minimal errors, eventually it may prove ineffective as the user may tire from repeated queries regarding accuracy of predicted emotions, such as when playing a video game that requires intense concentration. As such, as the AI model 170 matures through longer periods of training, a more indirect approach can be used to infer whether the predicted emotion is accurate or not.

Information regarding the accuracy of a predicted emotion as determined by the verification engine 355 may be fed back as training data 470 back into the AI model for purposes of updating the AI model. For example, when the feedback indicates that the predicted emotion is incorrect, then the solution set of possible emotions used for prediction can be reduced, such that the next iterative implementation of the AI model 170 to predict the emotion based on similarly captured multimodal cues will be more accurate. In that manner, the AI model 170 that is updated is able to output an updated predicted emotion, based on the same or updated set of multimodal cues.

Figure 5:
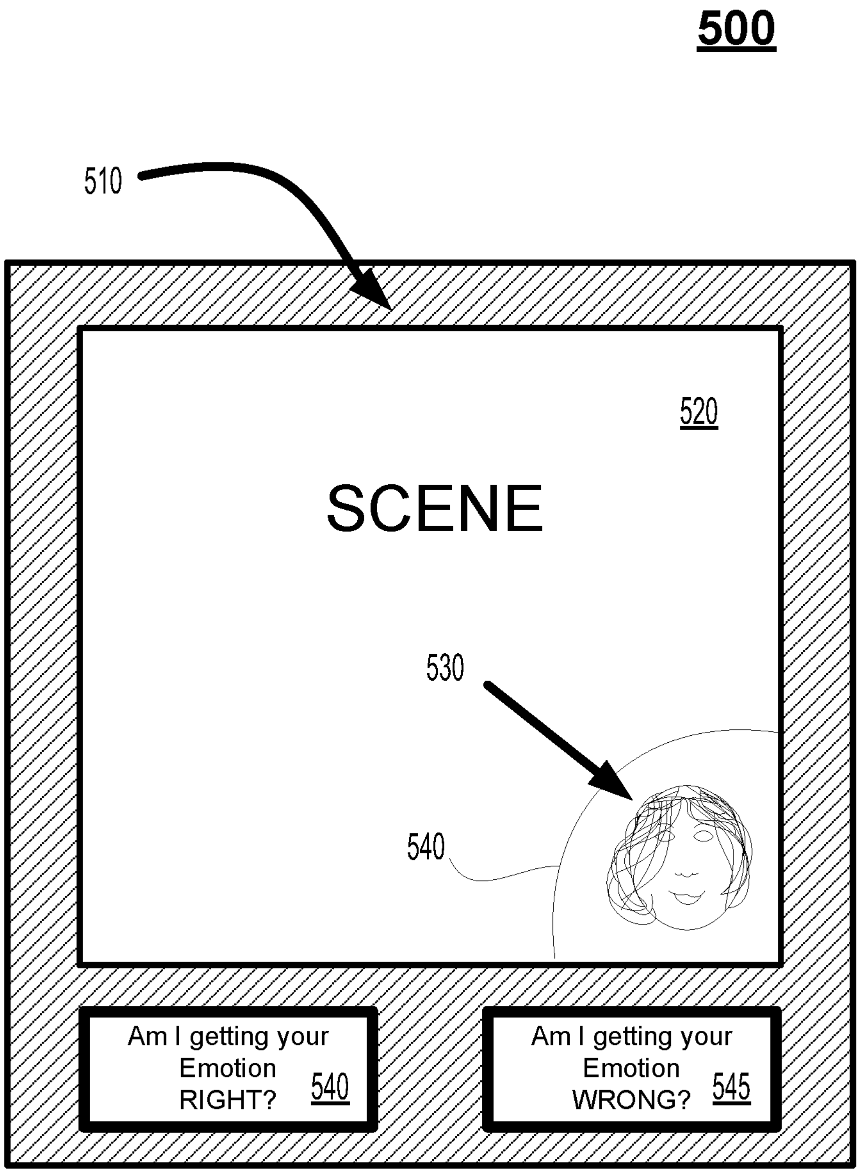
FIG. 5 illustrates a window including one or more visual cues indicating a predicted emotion of a user, in accordance with one embodiment of the present disclosure.

FIG. 5 illustrates a window 500 including one or more visual cues indicating a predicted emotion of a user that is interacting with an interaction application, and verification of the predicted emotion through a direct approach, in accordance with one embodiment of the present disclosure. Window 500 includes a presentation of a scene 520. While the user is interacting with the interaction application, a predicted emotion may be classified. Purely for example, the predicted emotion may indicate that the user is happy or satisfied. In one embodiment, an indirect visual cue may be provided that informs the user of the predicted emotion. That is, the user is presented with a representation of the predicted emotion. For example, a border 510 may be presented surrounding the scene 520, wherein the border is presented in a manner reflective of the happy emotion, such as being presented in a bright color (e.g., green, etc.), or may include objects indicating happiness (e.g., stars, hearts, etc.). In another example, an area 540 of the window 500 may be reserved to show a virtualized image 530 of the user that is reflective of the predicted emotion. For instance, the avatar 530 may be shown that is happy, wherein this avatar may also be presented to other users within a virtual environment. In that manner, the user is able to understand how his or her avatar is being presented to others.

In one embodiment, a direct approach to verifying the accuracy of the predicted emotion is shown in window 500. In particular, border 510 includes selection windows 540 and 545. Selection window 540 is used to directly query the user whether the predicted emotion is right or accurate, and selection of window 540 by the user indicates that the predicted emotion is accurate. Selection window 545 is used to directly query the user whether the predicted emotion is wrong or inaccurate, and selection of window 545 by the user indicates that the predicted emotion is inaccurate. The information through the selection of window 540 or 545 (e.g., indication of the accuracy of the predicted emotion) is provided as feedback to the AI model for training, wherein the AI model is updated based on the feedback.

Figure 6:
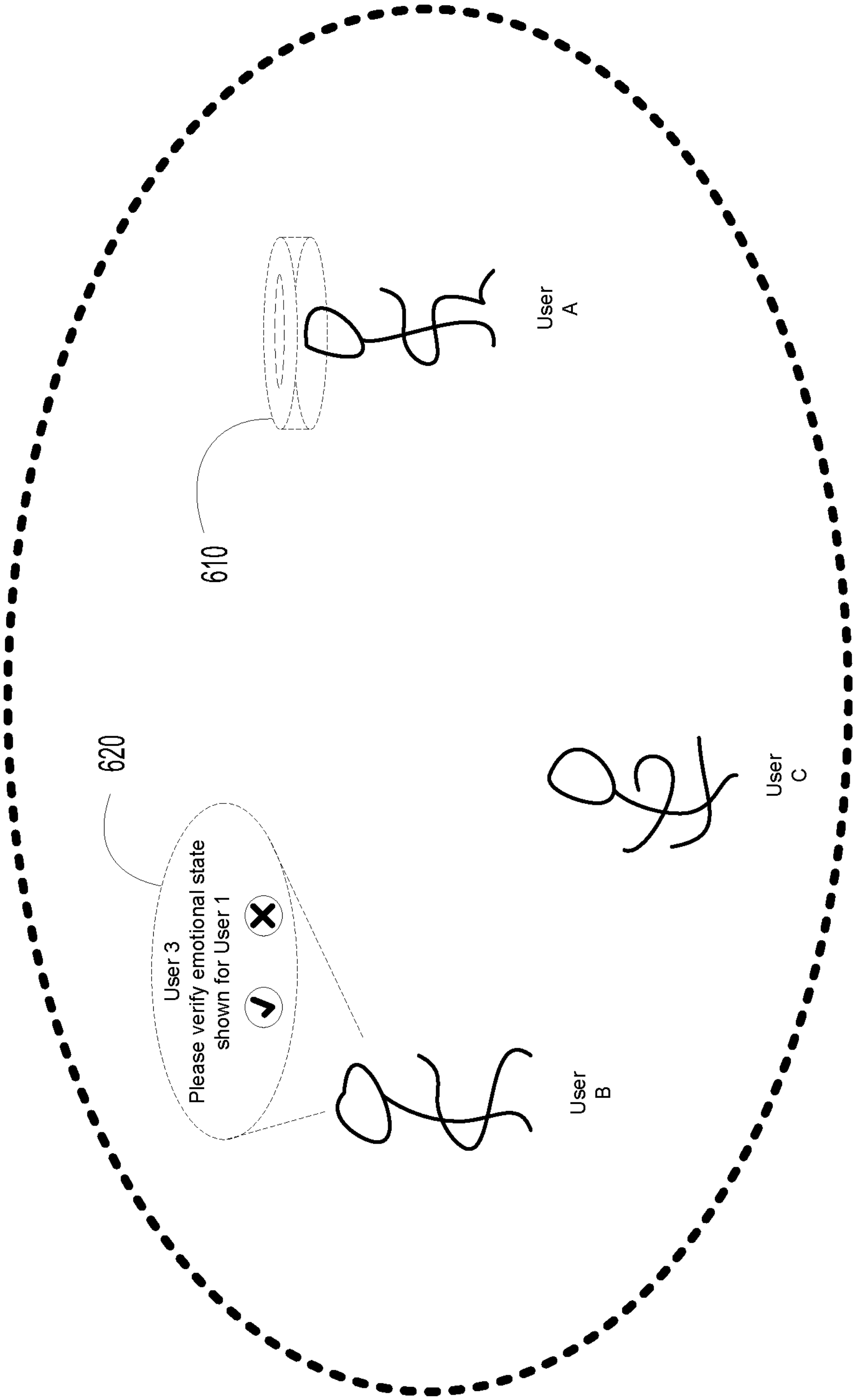
FIG. 6 illustrates a virtual environment generated by an interaction application, wherein the virtual environment includes a plurality of participants that can verify accuracy of an identified emotion of a particular participant, in accordance with one embodiment of the present disclosure.

FIG. 6 illustrates a virtual environment 600 generated by an interaction application, wherein the virtual environment includes a plurality of participants that can verify accuracy of an identified emotion of a particular participant, in accordance with one embodiment of the present disclosure. As shown, the plurality of participants includes at least user A, user B, and user C, wherein corresponding avatars of such users are presented in the virtual environment 600. A predicted emotion of user A is classified. Further, a representation 610 of the predicted emotion of user A is presented to the participants within the virtual environment 600 in association with an avatar of user A. For purposes of illustration, the representation may include a halo decorated in a suitable color, or shaped in a manner, or decorated with one or more objects and/or icons corresponding to the predicted emotion. The participants (other than user A) are queried whether the representation is correct or incorrect. Also, the participants may voluntarily provide information regarding accuracy of the predicted emotion of user A. For example, bubble 620 may be presented to user B asking for verification of the predicted emotion of user A. In addition, bubble 620 may include selection buttons that when selected indicate accuracy of the predicted emotion (i.e., accurate by checking the checkmark, or inaccurate by checking the "X" mark).

Figure 7:
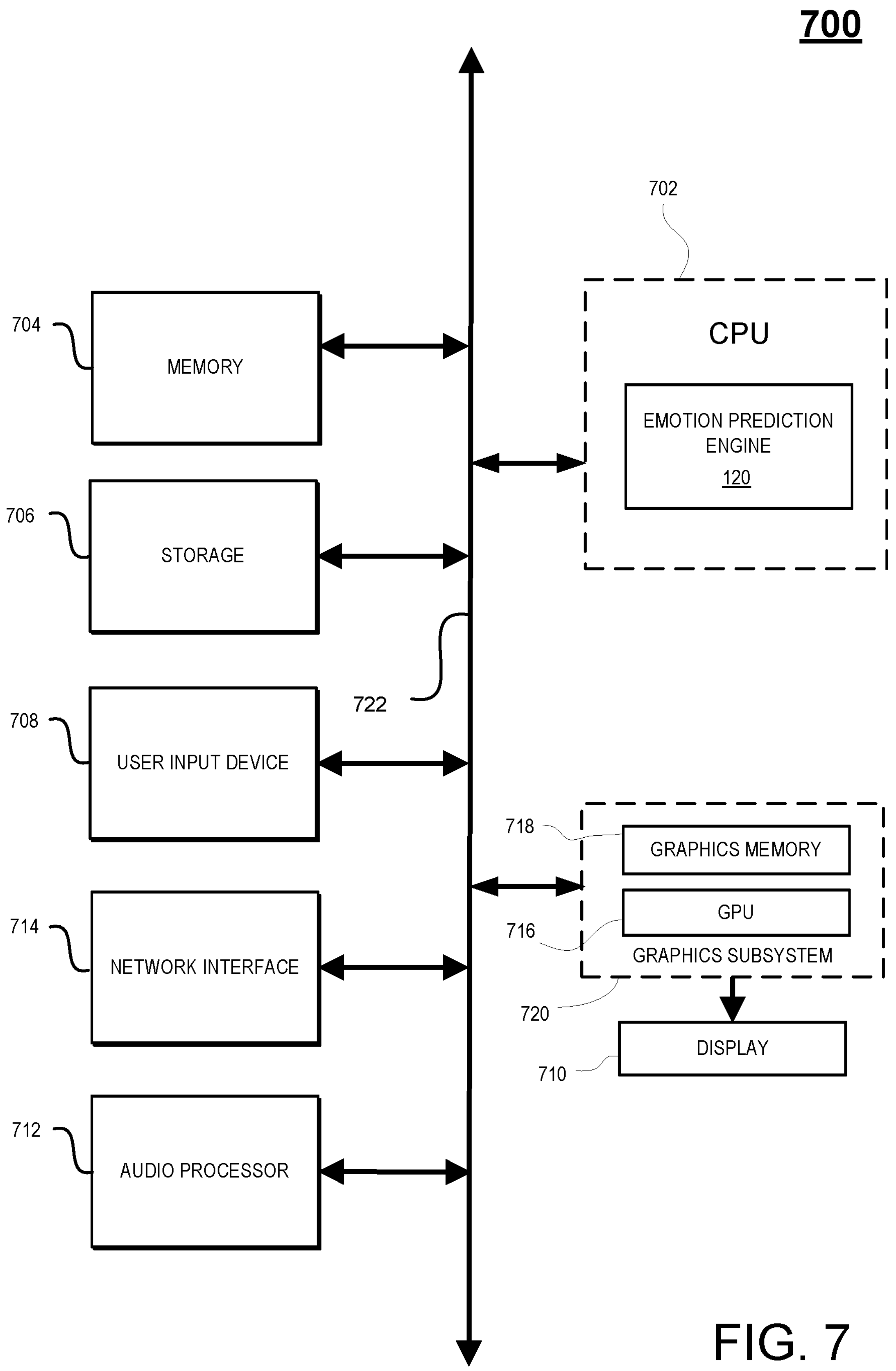
FIG. 7 illustrates components of an example device that can be used to perform aspects of the various embodiments of the present disclosure.

FIG. 7 illustrates components of an example device 700 that can be used to perform aspects of the various embodiments of the present disclosure. This block diagram illustrates a device 700 that can incorporate or can be a personal computer, video game console, personal digital assistant, a server or other digital device, and includes a central processing unit (CPU) 702 for running software applications and optionally an operating system. CPU 702 may be comprised of one or more homogeneous or heterogeneous processing cores. Further embodiments can be implemented using one or more CPUs with microprocessor architectures specifically adapted for highly parallel and computationally intensive applications.

In particular, CPU 702 may be configured to implement an emotion prediction engine 120 that is configured to classify and/or identify and/or predict emotion of a user using artificial intelligence, and the modification of content generated by an interaction application based on the predicted emotion. Verification of the identified emotion is provided as feedback for training and updating a model using the artificial intelligence that is configured to identify emotion of the user.

Memory 704 stores applications and data for use by the CPU 702. Storage 706 provides non-volatile storage and other computer readable media for applications and data and may include fixed disk drives, removable disk drives, flash memory devices, and CD-ROM, DVD-ROM, Blu-ray, HD-DVD, or other optical storage devices, as well as signal transmission and storage media. User input devices 708 communicate user inputs from one or more users to device 700, examples of which may include keyboards, mice, joysticks, touch pads, touch screens, still or video recorders/cameras, tracking devices for recognizing gestures, and/or microphones. Network interface 714 allows device 700 to communicate with other computer systems via an electronic communications network, and may include wired or wireless communication over local area networks and wide area networks such as the internet. An audio processor 712 is adapted to generate analog or digital audio output from instructions and/or data provided by the CPU 702, memory 704, and/or storage 706. The components of device 700 are connected via one or more data buses 722.

A graphics subsystem 720 is further connected with data bus 722 and the components of the device 700. The graphics subsystem 720 includes a graphics processing unit (GPU) 716 and graphics memory 718. Graphics memory 718 includes a display memory (e.g., a frame buffer) used for storing pixel data for each pixel of an output image. Pixel data can be provided to graphics memory 718 directly from the CPU 702. Alternatively, CPU 702 provides the GPU 716 with data and/or instructions defining the desired output images, from which the GPU 716 generates the pixel data of one or more output images. The data and/or instructions defining the desired output images can be stored in memory 704 and/or graphics memory 718. In an embodiment, the GPU 716 includes 3D rendering capabilities for generating pixel data for output images from instructions and data defining the geometry, lighting, shading, texturing, motion, and/or camera parameters for a scene. The GPU 716 can further include one or more programmable execution units capable of executing shader programs. In one embodiment, GPU 716 may be implemented within an AI engine (e.g., machine learning engine 190) to provide additional processing power, such as for the AI, machine learning functionality, or deep learning functionality, etc.

The graphics subsystem 720 periodically outputs pixel data for an image from graphics memory 718 to be displayed on display device 710. Display device 710 can be any device capable of displaying visual information in response to a signal from the device 700.

In other embodiments, the graphics subsystem 720 includes multiple GPU devices, which are combined to perform graphics processing for a single application that is executing on a CPU. For example, the multiple GPUs can perform alternate forms of frame rendering, including different GPUs rendering different frames and at different times, different GPUs performing different shader operations, having a master GPU perform main rendering and compositing of outputs from slave GPUs performing selected shader functions (e.g., smoke, river, etc.), different GPUs rendering different objects or parts of scene, etc. In the above embodiments and implementations, these operations could be performed in the same frame period (simultaneously in parallel), or in different frame periods (sequentially in parallel).

Accordingly, in various embodiments the present disclosure describes systems and methods configured for classifying emotion of a user using artificial intelligence, and the modification of content, generated by an interaction application in response to user input, and the dynamic updating of the artificial intelligence with feedback indicating accuracy of the predicted emotion.

It should be noted, that access services, such as providing access to games of the current embodiments, delivered over a wide geographical area often use cloud computing. Cloud computing is a style of computing in which dynamically scalable and often virtualized resources are provided as a service over the Internet. For example, cloud computing services often provide common applications (e.g., video games) online that are accessed from a web browser, while the software and data are stored on the servers in the cloud.

A game server may be used to perform operations for video game players playing video games over the internet, in some embodiments. In a multiplayer gaming session, a dedicated server application collects data from players and distributes it to other players. The video game may be executed by a distributed game engine including a plurality of processing entities (PEs) acting as nodes, such that each PE executes a functional segment of a given game engine that the video game runs on. For example, game engines implement game logic, perform game calculations, physics, geometry transformations, rendering, lighting, shading, audio, as well as additional in-game or game-related services. Additional services may include, for example, messaging, social utilities, audio communication, game play replay functions, help function, etc. The PEs may be virtualized by a hypervisor of a particular server, or the PEs may reside on different server units of a data center. Respective processing entities for performing the operations may be a server unit, a virtual machine, or a container, GPU, CPU, depending on the needs of each game engine segment. By distributing the game engine, the game engine is provided with clastic computing properties that are not bound by the capabilities of a physical server unit. Instead, the game engine, when needed, is provisioned with more or fewer compute nodes to meet the demands of the video game.

Users access the remote services with client devices (e.g., PC, mobile phone, etc.), which include at least a CPU, a display and I/O, and are capable of communicating with the game server. It should be appreciated that a given video game may be developed for a specific platform and an associated controller device. However, when such a game is made available via a game cloud system, the user may be accessing the video game with a different controller device, such as when a user accesses a game designed for a gaming console from a personal computer utilizing a keyboard and mouse. In such a scenario, an input parameter configuration defines a mapping from inputs which can be generated by the user's available controller device to inputs which are acceptable for the execution of the video game.

In another example, a user may access the cloud gaming system via a tablet computing device, a touchscreen smartphone, or other touchscreen driven device, where the client device and the controller device are integrated together, with inputs being provided by way of detected touchscreen inputs/gestures. For such a device, the input parameter configuration may define particular touchscreen inputs corresponding to game inputs for the video game (e.g., buttons, directional pad, gestures or swipes, touch motions, etc.).

In some embodiments, the client device serves as a connection point for a controller device. That is, the controller device communicates via a wireless or wired connection with the client device to transmit inputs from the controller device to the client device. The client device may in turn process these inputs and then transmit input data to the cloud game server via a network. For example, these inputs might include captured video or audio from the game environment that may be processed by the client device before sending to the cloud game server. Additionally, inputs from motion detection hardware of the controller might be processed by the client device in conjunction with captured video to detect the position and motion of the controller before sending to the cloud gaming server.

In other embodiments, the controller can itself be a networked device, with the ability to communicate inputs directly via the network to the cloud game server, without being required to communicate such inputs through the client device first, such that input latency can be reduced. For example, inputs whose detection does not depend on any additional hardware or processing apart from the controller itself can be sent directly from the controller to the cloud game server. Such inputs may include button inputs, joystick inputs, embedded motion detection inputs (e.g., accelerometer, magnetometer, gyroscope), etc.

Access to the cloud gaming network by the client device may be achieved through a network implementing one or more communication technologies. In some embodiments, the network may include 5th Generation (5G) wireless network technology including cellular networks serving small geographical cells. Analog signals representing sounds and images are digitized in the client device and transmitted as a stream of bits. 5G wireless devices in a cell communicate by radio waves with a local antenna array and low power automated transceiver. The local antennas are connected with a telephone network and the Internet by high bandwidth optical fiber or wireless backhaul connection. A mobile device crossing between cells is automatically transferred to the new cell. 5G networks are just one communication network, and embodiments of the disclosure may utilize earlier generation communication networks, as well as later generation wired or wireless technologies that come after 5G.

In one embodiment, the various technical examples can be implemented using a virtual environment via a head-mounted display (HMD), which may also be referred to as a virtual reality (VR) headset. As used herein, the term generally refers to user interaction with a virtual space/environment that involves viewing the virtual space through an HMD in a manner that is responsive in real-time to the movements of the HMD (as controlled by the user) to provide the sensation to the user of being in the virtual space or metaverse. An HMD can be worn in a manner similar to glasses, goggles, or a helmet, and is configured to display a video game or other metaverse content to the user. The HMD can provide a very immersive experience in a virtual environment with three-dimensional depth and perspective.

In one embodiment, the HMD may include a gaze tracking camera that is configured to capture images of the eyes of the user while the user interacts with the VR scenes. The gaze information captured by the gaze tracking camera(s) may include information related to the gaze direction of the user and the specific virtual objects and content items in the VR scene that the user is focused on or is interested in interacting with.

In some embodiments, the HMD may include an externally facing camera(s) that is configured to capture images of the real-world space of the user such as the body movements of the user and any real-world objects that may be located in the real-world space. In some embodiments, the images captured by the externally facing camera can be analyzed to determine the location/orientation of the real-world objects relative to the HMD. Using the known location/orientation of the HMD the real-world objects, and inertial sensor data from the, the gestures and movements of the user can be continuously monitored and tracked during the user's interaction with the VR scenes. For example, while interacting with the scenes in the game, the user may make various gestures (e.g., commands, communications, pointing and walking toward a particular content item in the scene, etc.). In one embodiment, the gestures can be tracked and processed by the system to generate a prediction of interaction with the particular content item in the game scene. In some embodiments, machine learning may be used to facilitate or assist in the prediction.

During HMD use, various kinds of single-handed, as well as two-handed controllers can be used. In some implementations, the controllers themselves can be tracked by tracking lights included in the controllers, or tracking of shapes, sensors, and inertial data associated with the controllers. Using these various types of controllers, or even simply hand gestures that are made and captured by one or more cameras, it is possible to interface, control, maneuver, interact with, and participate in the virtual reality environment or metaverse rendered on an HMD. In some cases, the HMD can be wirelessly connected to a cloud computing and gaming system over a network, such as internet, cellular, etc. In one embodiment, the cloud computing and gaming system maintains and executes the video game being played by the user. In some embodiments, the cloud computing and gaming system is configured to receive inputs from the HMD and/or interfacing objects over the network. The cloud computing and gaming system is configured to process the inputs to affect the game state of the executing video game. The output from the executing video game, such as video data, audio data, and haptic feedback data, is transmitted to the HMD and the interface objects.

Additionally, though implementations in the present disclosure may be described with reference to n HMD, it will be appreciated that in other implementations, non-HMDs may be substituted, such as, portable device screens (e.g., tablet, smartphone, laptop, etc.) or any other type of display that can be configured to render video and/or provide for display of an interactive scene or virtual environment. It should be understood that the various embodiments defined herein may be combined or assembled into specific implementations using the various features disclosed herein. Thus, the examples provided are just some possible examples, without limitation to the various implementations that are possible by combining the various elements to define many more implementations.

Embodiments of the present disclosure may be practiced with various computer system configurations including hand-held devices, microprocessor systems, microprocessor-based or programmable consumer electronics, minicomputers, mainframe computers and the like. Embodiments of the present disclosure can also be practiced in distributed computing environments where tasks are performed by remote processing devices that are linked through a wire-based or wireless network.

Although the method operations were described in a specific order, it should be understood that other housekeeping operations may be performed in between operations, or operations may be adjusted so that they occur at slightly different times or may be distributed in a system which allows the occurrence of the processing operations at various intervals associated with the processing, as long as the processing of the telemetry and game state data for generating modified game states and are performed in the desired way.

With the above embodiments in mind, it should be understood that embodiments of the present disclosure can employ various computer-implemented operations involving data stored in computer systems. These operations are those requiring physical manipulation of physical quantities. Any of the operations described herein in embodiments of the present disclosure are useful machine operations. Embodiments of the disclosure also relate to a device or an apparatus for performing these operations. The apparatus can be specially constructed for the required purpose, or the apparatus can be a general-purpose computer selectively activated or configured by a computer program stored in the computer. In particular, various general-purpose machines can be used with computer programs written in accordance with the teachings herein, or it may be more convenient to construct a more specialized apparatus to perform the required operations.

One or more embodiments can also be fabricated as computer readable code on a computer readable medium. The computer readable medium is any data storage device that can store data, which can be thereafter be read by a computer system. Examples of the computer readable medium include hard drives, network attached storage (NAS), read-only memory, random-access memory, CD-ROMs, CD-Rs, CD-RWs, magnetic tapes and other optical and non-optical data storage devices. The computer readable medium can include computer readable tangible medium distributed over a network-coupled computer system so that the computer readable code is stored and executed in a distributed fashion.

In one embodiment, the video game is executed either locally on a gaming machine, a personal computer, or on a server, or by one or more servers of a data center. When the video game is executed, some instances of the video game may be a simulation of the video game. For example, the video game may be executed by an environment or server that generates a simulation of the video game. The simulation, on some embodiments, is an instance of the video game. In other embodiments, the simulation maybe produced by an emulator that emulates a processing system.

Although the foregoing embodiments have been described in some detail for purposes of clarity of understanding, it will be apparent that certain changes and modifications can be practiced within the scope of the appended claims. Accordingly, the present embodiments are to be considered as illustrative and not restrictive, and the embodiments are not to be limited to the details given herein, but may be modified within the scope and equivalents of the appended claims.

What is claimed is:

1. A method, comprising:

receiving an input from a user for an interaction application during execution of the interaction application;

receiving a plurality of cues from a plurality of trackers, wherein each tracker of the plurality of trackers is configured to generate a respective cue using artificial intelligence (AI);

providing the plurality of cues to an AI model that is configured to receive input including one or more cues and to generate output including a classification of at least one emotion based on the one or more cues;

obtaining, as output from the AI model, a predicted emotion of the user;

generating initial content for the interaction application in response to the input from the user, wherein the initial content comprises a user interface having a first complexity level;

determining, based on the predicted emotion of the user, a modification to be made to the initial content, the modification including an overlay;

generating the overlay; and applying the overlay to the initial content to generate modified content for the interaction application, wherein applying the overlay to the initial content changes the first complexity level of the user interface such that the modified content comprises a modified user interface having a second complexity level that is different from the first complexity level.

2. The method of claim 1, wherein the interaction application comprises a video game, the modification including a modified game parameter in the video game, wherein the modified game parameter is used when executing the video game based on the input from the user.

3. The method of claim 1, wherein:

the input includes a communication from the user to a target user, the initial content includes a translation of the communication, the modification includes a modified translation of the communication, and the modified translation is delivered to a device of the target user.

4. The method of claim 1, further comprising:

verifying inaccuracy of the predicted emotion; and providing feedback to the AI model indicating that the predicted emotion is inaccurate for training the AI model, wherein the AI model is updated based on the feedback.

5. The method of claim 4, wherein the plurality of cues comprises a first plurality of cues, the predicted emotion comprises a first predicted emotion, and verifying the inaccuracy of the first predicted emotion includes:

receiving a second plurality of cues from a plurality of trackers within a specified time period following receipts of the first plurality of cues;

providing the second plurality of cues to the AI model to obtain a second predicted emotion; and determining an inconsistency between the first predicted emotion and the second predicted emotion.

6. The method of claim 4, wherein the verifying the inaccuracy of the predicted emotion includes:

determining that the predicted emotion has a low degree of confidence; and directly querying the user as to whether the predicted emotion is accurate.

7. The method of claim 1, further comprising:

verifying accuracy of the predicted emotion;

presenting to the user a first option and a second option;

receiving a selection of the first option or the second option from the user; and inferring a positive relationship between the predicted emotion and the selection, wherein a subsequent selection between the first option and the second option is used to determine accuracy of a subsequent predicted emotion based on the positive relationship between the predicted emotion and the selection.

8. The method of claim 1, wherein applying the overlay to the initial content comprises incorporating the overlay into one or more video frames of the initial content.

9. The method of claim 1, wherein generating the overlay is performed by an overlay engine of the interaction application.

10. The method of claim 1, wherein the modified content is output by the interaction application for display by a device of the user.

11. A non-transitory computer-readable medium storing a computer program for performing a method, the computer-readable medium comprising:

program instructions for receiving an input from a user for an interaction application during execution of the interaction application;

program instructions for receiving a first plurality of cues from a plurality of trackers, wherein each tracker of the plurality of trackers is configured to generate a respective cue using artificial intelligence (AI);

program instructions for providing the plurality of cues to an AI model that is configured to receive input including one or more cues and to generate output including a classification of at least one emotion based on the one or more cues;

program instructions for obtaining, from the AI model, a predicted emotion of the user;

program instructions for generating initial content for the interaction application in response to the input from the user, wherein the initial content comprises a user interface having a first complexity level;

program instructions for determining, based on the predicted emotion of the user, a modification to be made to the initial content, the modification including an overlay;

program instructions for generating the overlay; and program instructions for applying the overlay to the initial content generate modified content for the interaction application, wherein applying the overlay to the initial content changes the first complexity level of the user interface such that the modified content comprises a modified user interface having a second complexity level that is different from the first complexity level.

12. The non-transitory computer-readable medium of claim 11, wherein the interaction application comprises a video game, the modification including a modified game parameter in the video game, wherein the modified game parameter is used when executing the video game based on the input from the user.

13. The non-transitory computer-readable medium of claim 11, wherein:

the input includes a communication from the user to a target user, the initial content includes a translation of the communication, the modification includes a modified translation of the communication, and the modified translation is delivered to a device of the target user.

14. The non-transitory computer-readable medium of claim 11, further comprising:

program instructions for verifying inaccuracy of the predicted emotion; and program instructions for providing feedback to the AI model indicating that the predicted emotion is inaccurate for training the AI model, wherein the AI model is updated based on the feedback.

15. The non-transitory computer-readable medium of claim 11, further comprising:

program instructions for verifying accuracy of the predicted emotion;

program instructions for presenting to the user a first option and a second option;

program instructions for receiving a selection of the first option or the second option from the user; and program instructions for inferring a positive relationship between the predicted emotion and the selection, wherein a subsequent selection between the first option and the second option is used to determine accuracy of a subsequent predicted emotion based on the positive relationship between the predicted emotion and the selection.

16. A computer system comprising:

a processor;

memory coupled to the processor and having stored therein instructions that, if executed by the computer system, cause the computer system to execute a method, comprising:

receiving an input from a user for an interaction application during execution of the interaction application;

receiving a plurality of cues from a plurality of trackers, wherein each tracker of the plurality of trackers is configured to generate a respective cue using artificial intelligence (AI);

providing the plurality of cues to an AI model that is configured to receive input including one or more cues and to generate output including a classification of at least one emotion based on the one or more cues;

obtaining, as output from the AI model, a predicted emotion of the user;

generating initial content for the interaction application in response to the input from the user, wherein the initial content comprises a user interface having a first complexity level;

determining, based on the predicted emotion of the user, a modification to be made to the initial content, the modification including an overlay;

generating the overlay; and applying the overlay to the initial content to generate modified content for the interaction application, wherein applying the overlay to the initial content changes the first complexity level of the user interface such that the modified content comprises a modified user interface having a second complexity level that is different from the first complexity level.

17. The computer system of claim 16, wherein the interaction application comprises a video game, the modification including a modified game parameter in the video game, wherein the modified game parameter is used when executing the video game based on the input from the user.

18. The computer system of claim 16, wherein:

the input includes a communication from the user to a target user, the initial content includes a translation of the communication, the modification includes a modified translation of the communication, and the modified translation is delivered to a device of the target user.

19. The computer system of claim 16, the method further comprising:

verifying inaccuracy of the predicted emotion; and providing feedback to the AI model indicating that the predicted emotion is inaccurate for training the AI model, wherein the AI model is updated based on the feedback.

* * * * *